US008621778B2

(12) United States Patent
Conventry (10) Patent No.: US 8,621,778 B2
(45) Date of Patent: Jan. 7, 2014

(54) MODULATOR (75) Inventor: Andrew Conventry, Burleigh Heads (AU)

(73) Assignee: Bantix Worldwide Pty Ltd, Queensland (AU)

( * ) Notice: Subject to any disclaimer, the term of this patent is extended or adjusted under 35 U.S.C. 154(b) by 396 days.

(21) Appl. No.: 13/056,630

(22) Filed: Jan. 28, 2011

(65) Prior Publication Data
US 2011/0167711 A1    Jul. 14, 2011

Related U.S. Application Data (63) Continuation of application No. PCT/AU2009/000964, filed on Jul. 29, 2009.

(30) Foreign Application Priority Data

Jul. 29, 2008 (AU) .............................. 2008903857

(51) Int. Cl.
*A01M 1/20* (2006.01)
(52) U.S. Cl.
USPC ............................................. 43/107; 137/82
(58) Field of Classification Search
USPC ...................................... 43/107, 122; 137/82
See application file for complete search history.

(56) References Cited

U.S. PATENT DOCUMENTS

| 3,052,217 | A | * | 9/1962 | Bunker et al. ................... 91/165 |
| 4,037,351 | A |   | 7/1977 | Springer |
| 5,657,576 | A | * | 8/1997 | Nicosia ......................... 43/132.1 |
| 6,088,949 | A | * | 7/2000 | Nicosia et al. ................... 43/107 |
| 6,209,256 | B1 |   | 4/2001 | Brittin et al. |
| 6,817,140 | B1 | * | 11/2004 | Durand et al. ................... 43/139 |
| 6,898,896 | B1 |   | 5/2005 | McBride et al. |
| 7,320,459 | B2 |   | 1/2008 | Johns |
| 2005/0210737 | A1 | * | 9/2005 | Durand et al. ................... 43/139 |
| 2007/0011940 | A1 | * | 1/2007 | Chen et al. ....................... 43/113 |

FOREIGN PATENT DOCUMENTS

| AU | 199944477 A1 | 3/2000 |
| CN | 1059823 A | 4/1992 |

* cited by examiner

*Primary Examiner* — Christopher P Ellis
(74) *Attorney, Agent, or Firm* — Schwabe, Williamson & Wyatt, P.C.

(57) ABSTRACT

A modulator (10, 10A) for changing a constant flow of gas to a pulsed or intermittent flow of gas, said modulator (10, 10A) including a housing component (11) and an insertion tube (15) for insertion into a hollow interior (16) of the housing component (11) wherein after insertion of the insertion tube (15) into the housing component (11), gas is generated either in situ within the hollow interior (16) of the housing component (11) and be caused to flow out of an outlet (23A) of the modulator (10, 10A) in pulses or alternatively gas is passed into the insertion tube (15) in a constant flow and upon reaching the hollow interior (16) of the housing component (11) is released therefrom through the outlet (23A) in a pulsed flow.

19 Claims, 12 Drawing Sheets

DETAIL A
FIG. 11

MODULATOR

CROSS REFERENCE TO RELATED APPLICATIONS

The present application is a national phase entry of, and claims priority under 35 U.S.C. §371 to, International Patent Application No. PCT/AU2009/000964, filed 29 Jul. 2009, entitled "Modulator," which designates the United States of America, and which claims priority to Australian Patent Application No. 2008903857, filed 29 Jul. 2008, the entire content and disclosure of which are hereby incorporated by reference in their entirety.

FIELD OF INVENTION

This invention relates to a modulator for changing a constant flow of gas to a pulsed or intermittent flow of gas and has particular reference to generation of carbon dioxide or volatile lures for attracting biting or flying insects inclusive of mosquitoes.

Reference may be made to U.S. Pat. No. 6,817,140 which refers to a flying insect trapping device configured to be used with hydrocarbon gas such as propane wherein the propane is passed through a regulator device for controlling flow of gas in intermittent pulses. The flow regulator is in the form of a solenoid that is programmed by a controller to convert a continuous flow of gas to a pulsed or intermittent flow of gas. There was also provided a valve for flushing of the solenoid and a fuel delivery nozzle when required. The pulsed flow of propane was passed through a catalylic convertor device to convert the propane to carbon dioxide which was used to attract mosquitoes to the trapping device.

Reference may also be made to Patent Publication WO/2005/108244 which describes a process for the catalytic oxidation of hydrocarbon gas which comprises releasing pulses of a compressed hydrocarbon gas into an expansion chamber and passing the expanding hydrocarbon gas over a catalytic convertor to oxidize the hydrocarbon gas.

The aforementioned prior art is exemplary of the fact that changing a flow of gas from a constant flow to a pulsed intermittent flow is not new.

However, such prior art has no relevance to the present invention which refers to a modulator of simple construction and which is efficient in use which has particular reference to generation of a pulsed flow of carbon dioxide, although the modulator may be utilized to provide a pulsed flow of other gases.

An object of the invention therefore is to provide a modulator for changing a flow of gas from a constant flow to a pulsed or intermittent flow which is simple in construction and effective in operation.

The modulator of the invention includes a housing component and an insertion tube flow of gas to a pulsed or intermittent flow of gas, said modulator including a housing component and an insertion tube for insertion into a hollow interior of the housing component wherein after insertion of the insertion tube into the housing component, gas is generated either in situ within the hollow interior of the housing component and be caused to flow out of an outlet of the modulator in pulses or alternatively gas is passed into the insertion tube in a constant flow and upon reaching the hollow interior of the housing component is released therefrom through the outlet in a pulsed flow.

The housing component is preferably a hollow tube having one closed bottom end and an open upper end in use. The housing component in one embodiment may contain an attractant medium for attracting insects which preferably generates carbon dioxide or other volatile lure for insects in situ.

However, more generally the housing component may include a viscous fluid such as glycerine, a mixture of water and glycerine, honey, molasses or syrups of various kinds including maple syrup and chocolate syrup. Suitably since viscous fluid may have a viscosity of 500-30,000 cP.

The attractant medium for insertion into the housing component suitably is formed of food grade components and is responsible for causing a generation of a volatile insect lure such as a carbon dioxide for exiting the modulator in a pulsed intermittent flow as hereinafter described. Various preferred forms of attractant medium will also be described hereinafter.

The open end of the hollow tube may have a lid or cover releasably attached to the open end for preventing escape of the carbon dioxide or volatile lure when not in use.

The insertion tube may also have an elongate body which preferably tapers outwardly from top to bottom in use. The insertion tube may have a bottom open end. The insertion tube may have an enlarged top end which has a plurality of ribs having spaces or gaps therebetween in flow communication with a hollow interior of the insertion tube for releasing gas from the modulator in a pulsed intermittent flow.

Reference may be made to a preferred embodiment of the invention as shown in the attached drawings wherein.

Figure 1:
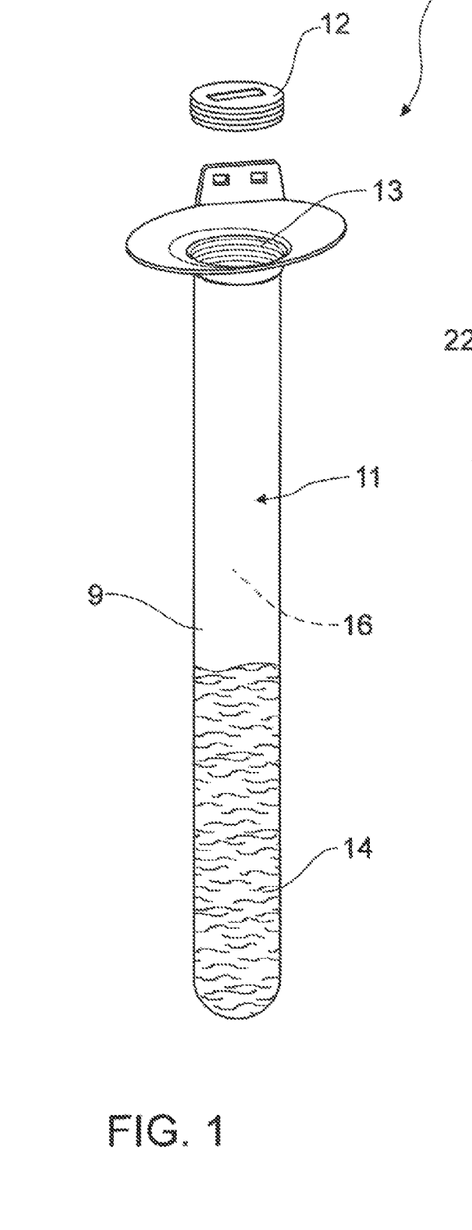
FIG. 1 is a perspective view of a modulator housing component adapted to contain a food grade ingredient adapted to attract insects.
Figure 2:
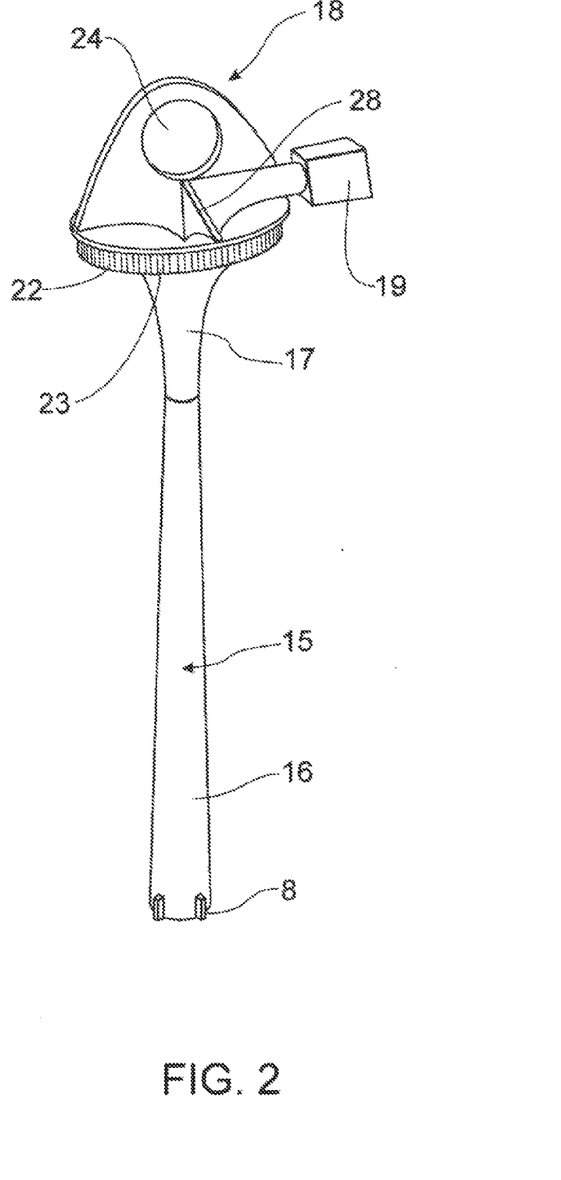
FIG. 2 is a perspective view of a modulator insertion component adapted to be inserted into the modulator housing component shown in FIG. 1.

In FIGS. 1-2 of the drawings there is shown modulator 10 having a housing component 11 and an insertion component 15. The housing component 11 has a screw top 12 which engages with a corresponding screw threaded portion 13. Housing component 11 also has body 9, hollow interior 16 and food grade insect attractant or viscous fluid 14 located in hollow interior 16. The screw top 12 is necessary for preventing escape of volatiles from the food grade attractant from housing component 11 and is used when housing component 11 is separated from insertion component 15.

Figure 3:
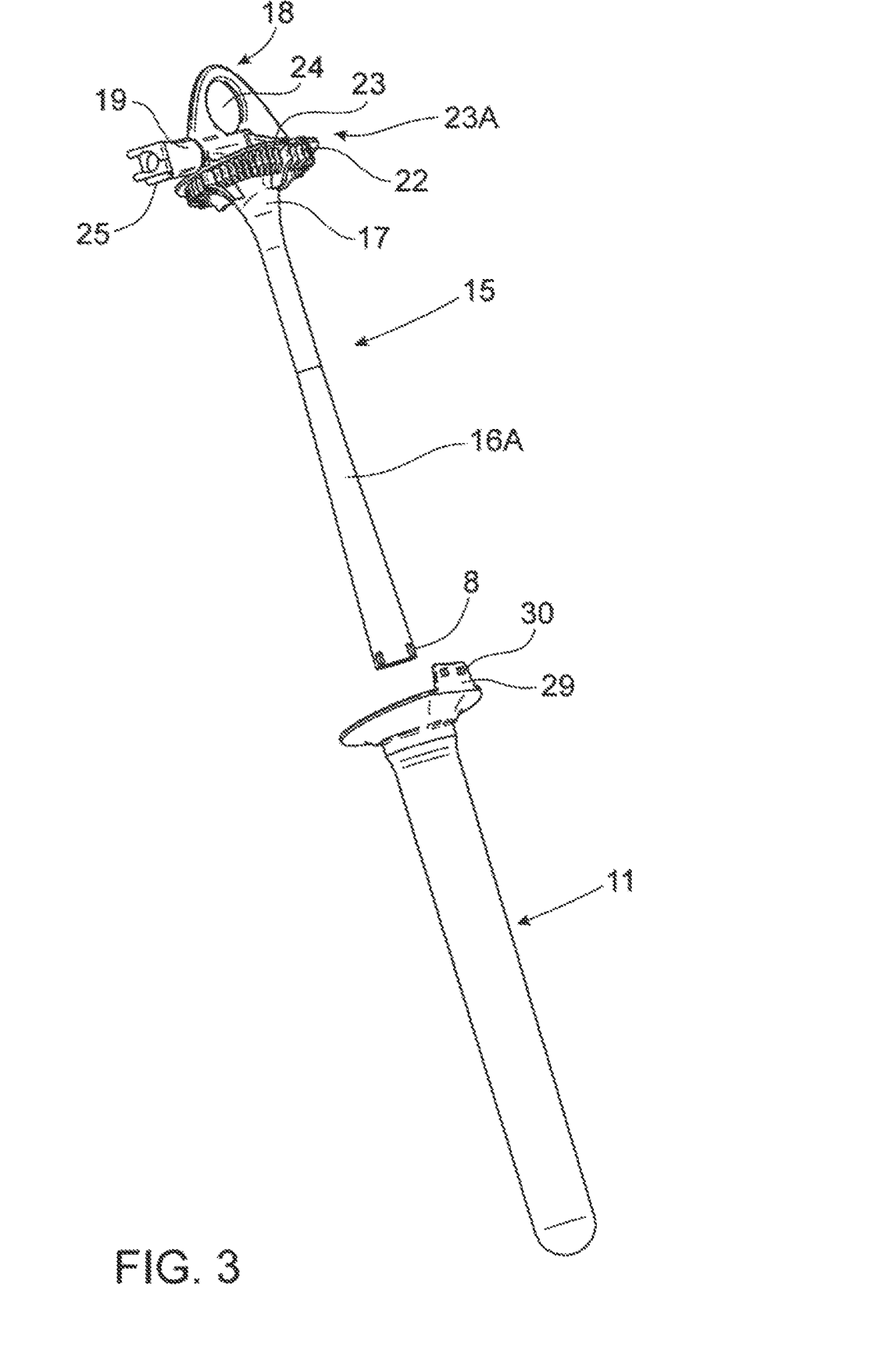
FIG. 3 shows an exploded perspective view of the modulator of the invention showing the insertion component about to be inserted into the housing component.
Figure 4:
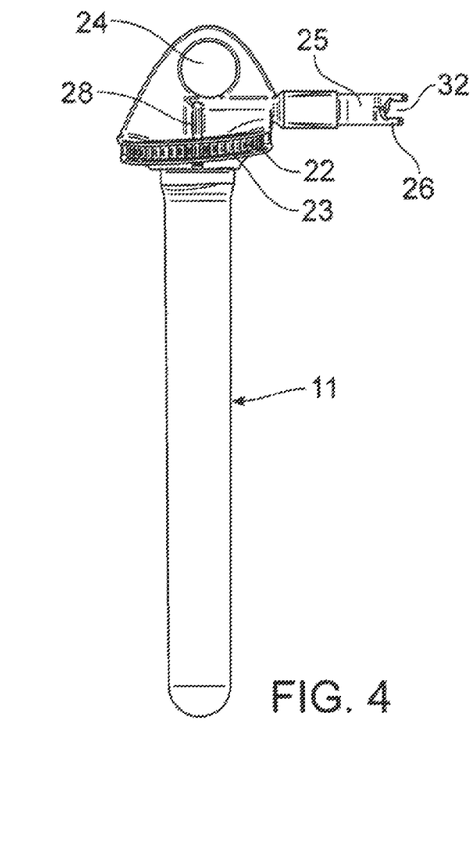
FIGS. 4-6 show assembled views of the components of FIG. 3 from various angles.

The insertion component 15 shown in FIGS. 2-6 has body 16A which tapers outwardly from top to bottom as shown, locating tabs 8, and neck portion 17. There is also provided top end part 18 having finger aperture 24, ribs 22 separated by spaces 23, socket lug 19 for engagement with a gas outlet fitting 20 of a gas hose 21 shown in FIG. 7 and reinforcing ribs 28. Housing component 11 is also provided with a projection 29 having locating apertures 30 which engage with corresponding tabs 31 shown in FIGS. 5-6 when insertion component 15 is inserted in housing component 11. There is also provided as best shown in FIG. 4 a retaining clip 25 for engagement with gas hose 21 which has resilient fingers 26 surrounding an aperture 32 which engages with gas hose 21 in use as shown in FIG. 7.

Figure 5:
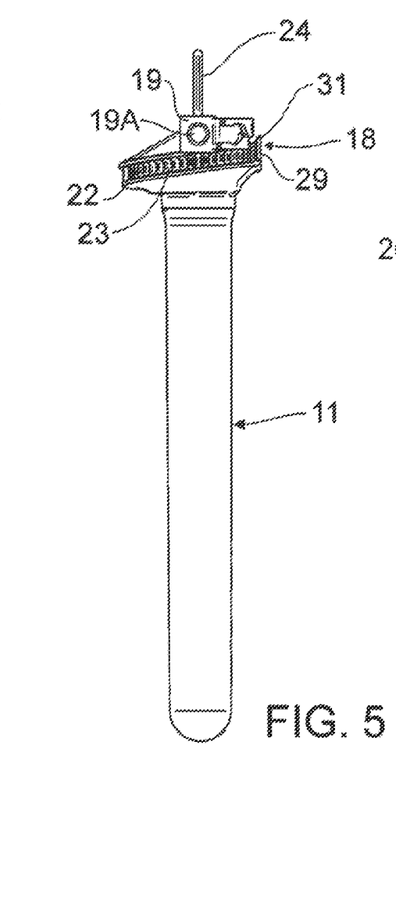
Figure 6:
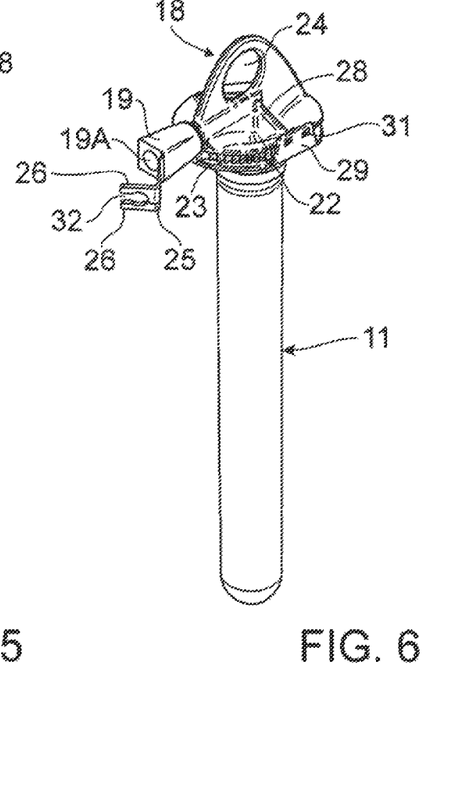

FIG. 3 shows how insertion component 15 is inserted into housing component 11 and FIGS. 4-6 show an assembled view of insertion component 15 in housing component 11.

Figure 7:
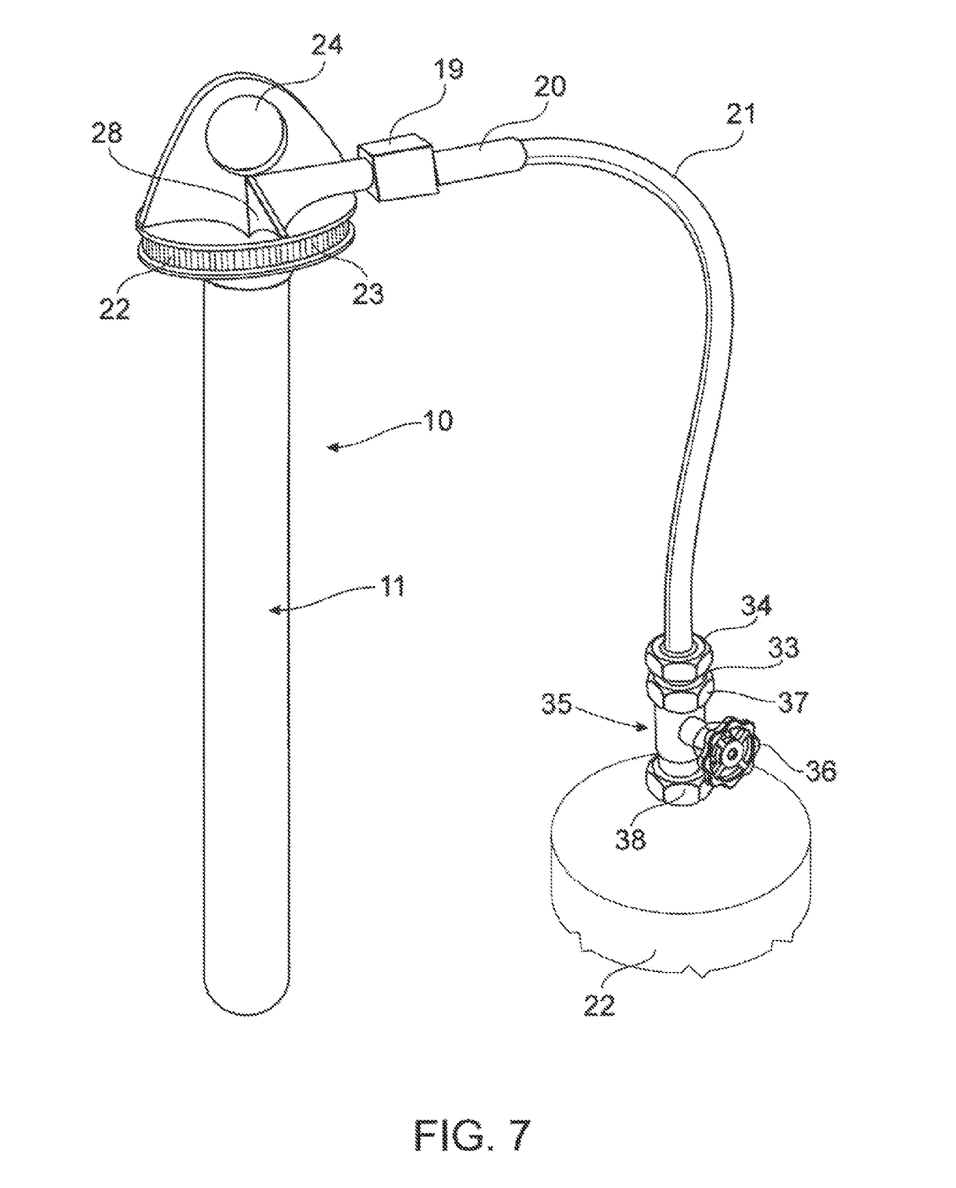
FIG. 7 shows an assembled view of the components of FIG. 3 with the insertion member connected to a source of carbon dioxide.

In FIG. 7 there is shown a modulator 10 connected to gas bottle 22 wherein sleeve 33 and integral nut 34 are screw threadedly attached to a mating screw threaded bore (not shown) in gas fitting 35 of gas bottle 22.

There is also provided an adjustment handle 36 for switching gas flow on/off from bottle 22 as well as nuts 37 and 38 of gas outlet fitting 35.

Figure 8:
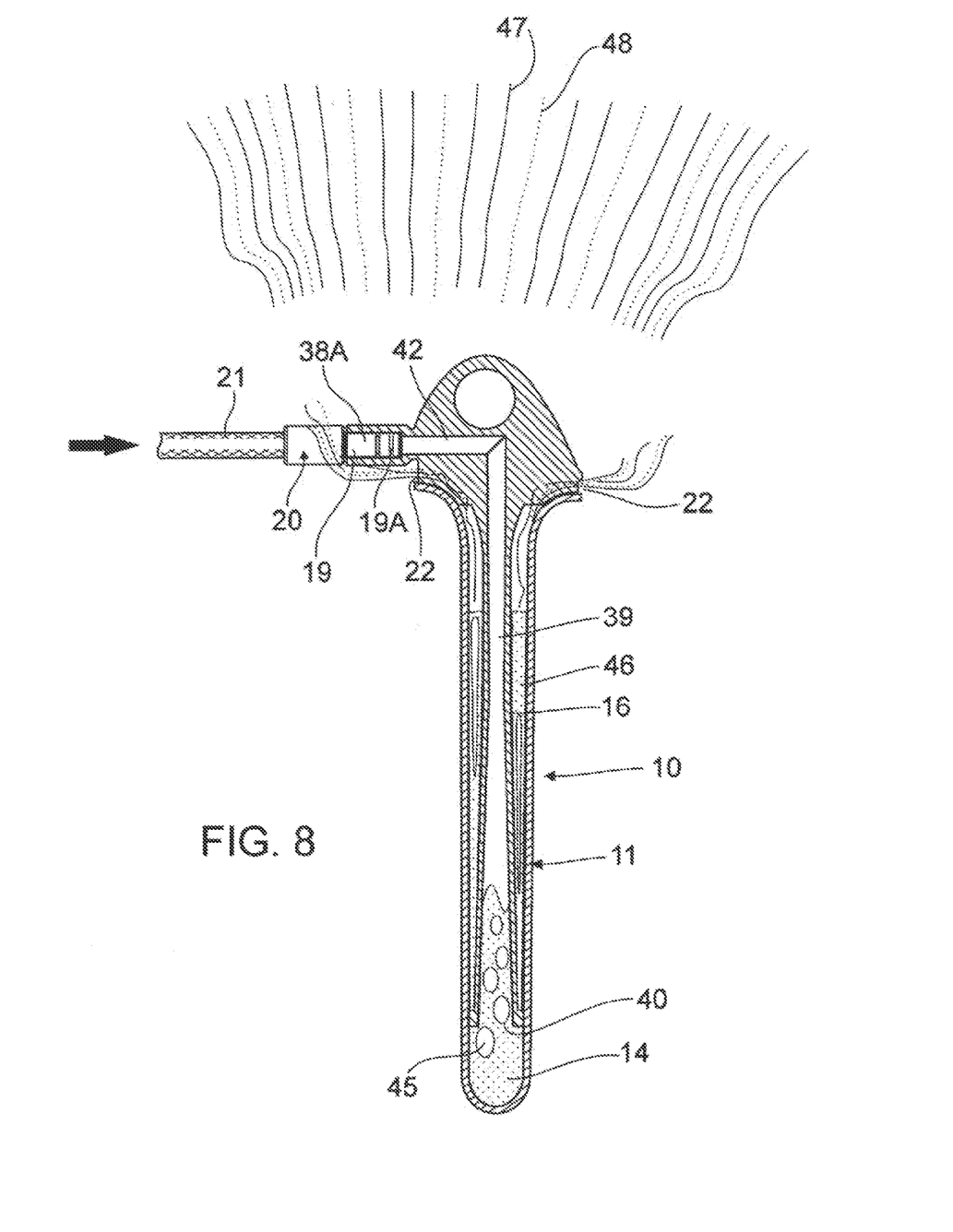
FIG. 8 shows the pulsing effect produced by carbon dioxide being released under pressure into the modulator housing component containing the food grade attractant at an initial period of time.

In FIG. 8 it is noted that gas outlet fitting 20 has a hollow spigot 38A inserted into recess 19A of socket lug 19 and thus gas flows from gas bottle 22 through gas hose 21 to hollow bore 39 of insertion component 15 which is tubular as shown having an open lower end 40. The gas flows through horizontal branch passage 42 to hollow bore 39 and then mixes with food grade attractant or viscous medium 14 as shown. The gas is carbon dioxide and flow through hollow bore 39 is continuous. It has been established scientifically that female mosquitoes are more attracted to intermittent plumes or pulses of $CO_2$ rather than a continuous flow of gas since pulsing mimics the breathing pattern of mammals.

A primary function of modulator 10 is to pulse carbon dioxide for the purpose of attracting mosquitoes and other biting insects to a suitable trap shown hereinafter in FIGS. 10-11.

It will be appreciated that modulator 10 can operate without connection to a gas regulator hose in order to function solely as a dispenser of a particular lure or attractant blend 14. In this capacity the modulator 10 can function as a decoy to lure insects away from areas where people gather. When used as a lure dispenser the modulator 10 can be attached to a mosquito trap or located adjacent thereto.

The modulator 10 contains a proprietary food grade medium or a viscous fluid 14 which causes the flow of gas passing through it to pulse. This medium 14 can be varied to produce a faster or slower pulse rate and to change the volume of each release of gas.

Select food grade constituents that singly or collectively are attractants to the target insect or other life form can be added to the medium 14 in whatever proportions are required for the specific application. An amount of lure will be released along with the gas to form a gas-lure mixture.

The use of a gas hose 21 having a ceramic insert and associated capillary passage as described in International Patent Publication WO 2009/003246 which is totally incorporated herein by reference enables micro control of the flow of gas from a pressurized cylinder 22 without the need of a conventional regulator. This means extremely low flows of gas can be achieved resulting in extended time between refills of a gas bottle and better economy for the user.

When more flow is required in a specific application one option is to use a proprietary gas hose with a higher flow rate. However, as stated above, gas usage increases and the economics of gas usage are affected.

In order to produce sufficient output of carbon dioxide for the specific application while maintaining economy the medium 14 can include suitable food grade constituents that will with the aid of natural moisture contained in the medium produce a certain amount of carbon dioxide to supplement the low flow of gas from the gas regulator hose connected to the pressurized cylinder 22. The modulator 10 functions as a reactor in this case while still emitting other lures contained therein and continuing to pulse the carbon dioxide.

This combined supply of carbon dioxide as described above provides a very economical approach.

The modulator 10 can be made of any suitable material and be of any suitable size. It can be a permanent device that can be refilled or it can be a throwaway.

In FIG. 8 it will be noted that after the $CO_2$ has mixed with the attractant medium 14 pulses or bubbles or plumes 45 are generated which then exit through spaces 22 of outlet 23A shown in FIG. 2 and between ribs 23 as shown after passage through flow passage 46 between inner tube or body 16 and housing 11. It will also be appreciated that such plumes 45 are represented in gaseous form above modulator 10 wherein carbon dioxide is represented by lines 47 in solid outline entrained with a volatile attractant lure 48 shown in phantom.

Figure 9:
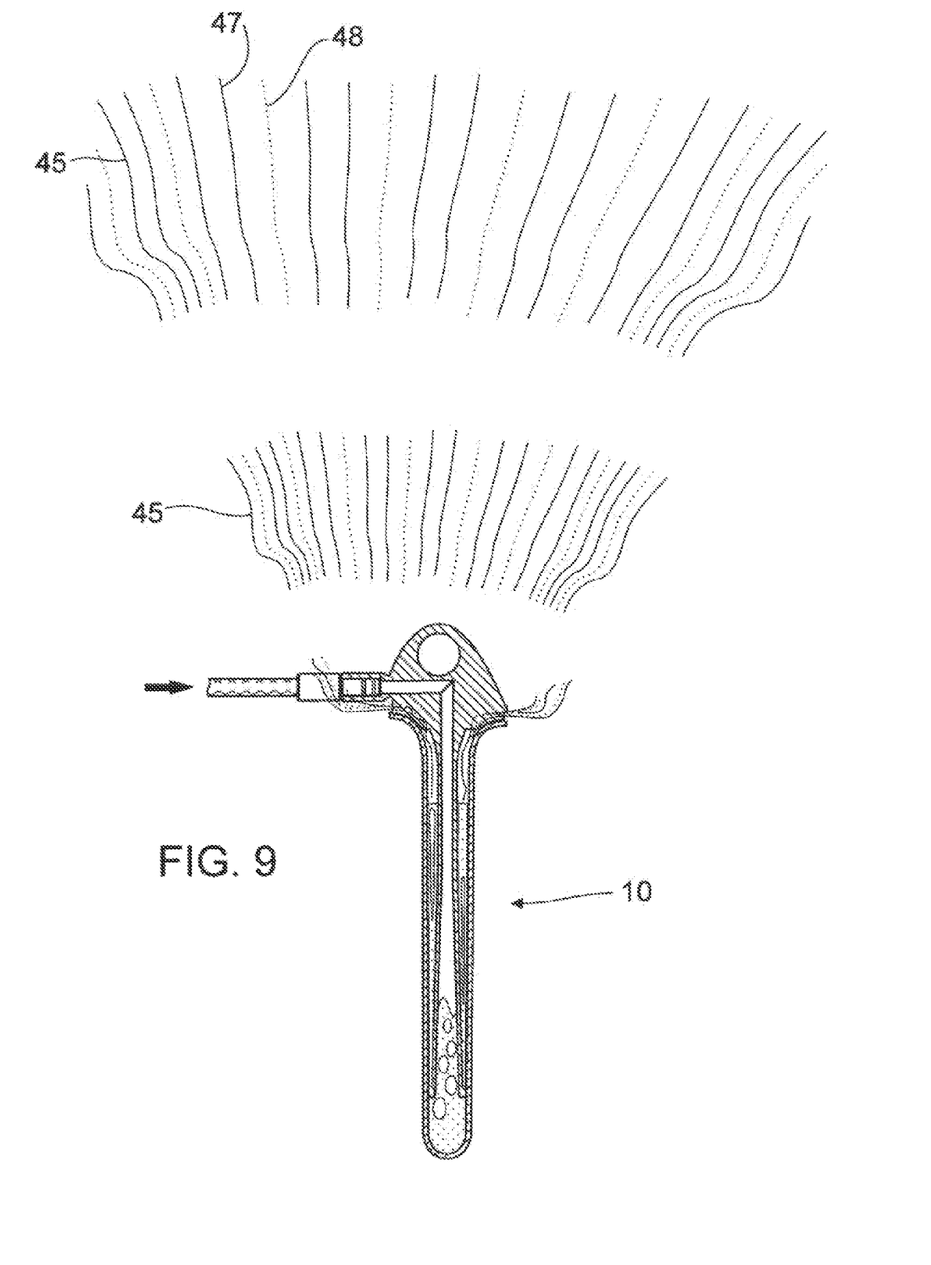
FIG. 9 shows a similar view to FIG. 8 at a later period of time.

FIG. 9 shows a similar view to FIG. 8 but showing generation of successive plumes 45 which are especially successful in attracting mosquitoes because they simulate human breathing.

Figure 10:
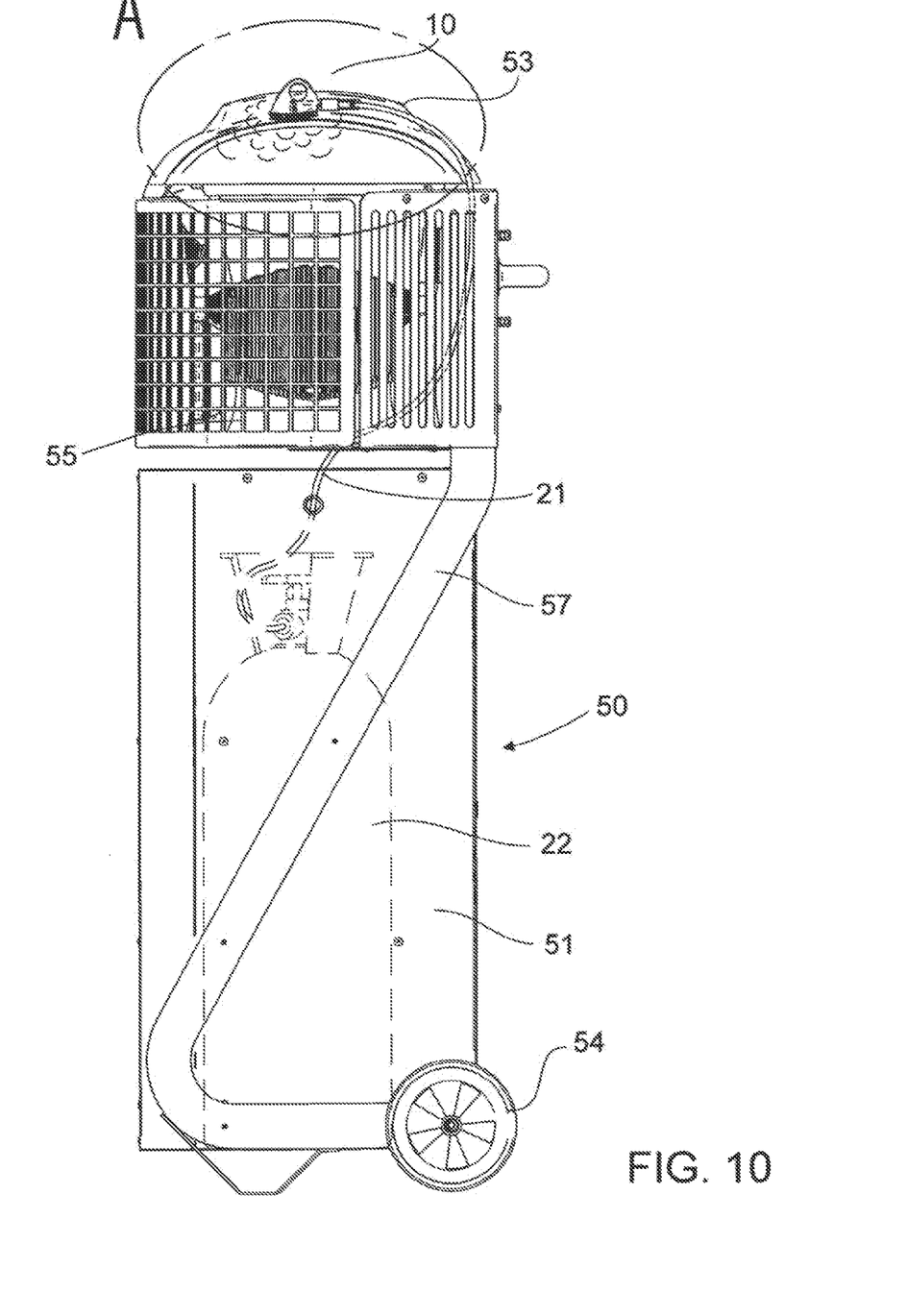
FIG. 10 shows the modulator attached to an insect tray.

In FIG. 10 there is shown a mosquito trap 50 supported on a trolley 51 also supports gas bottle 22. There is shown modulator 10 attached to a top surface 53 of mosquito trap 50. Trolley 51 is supported on wheels 54. Gas hose 21 is also connected to gas bottle 22 as well as modulator 10.

Figure 11:
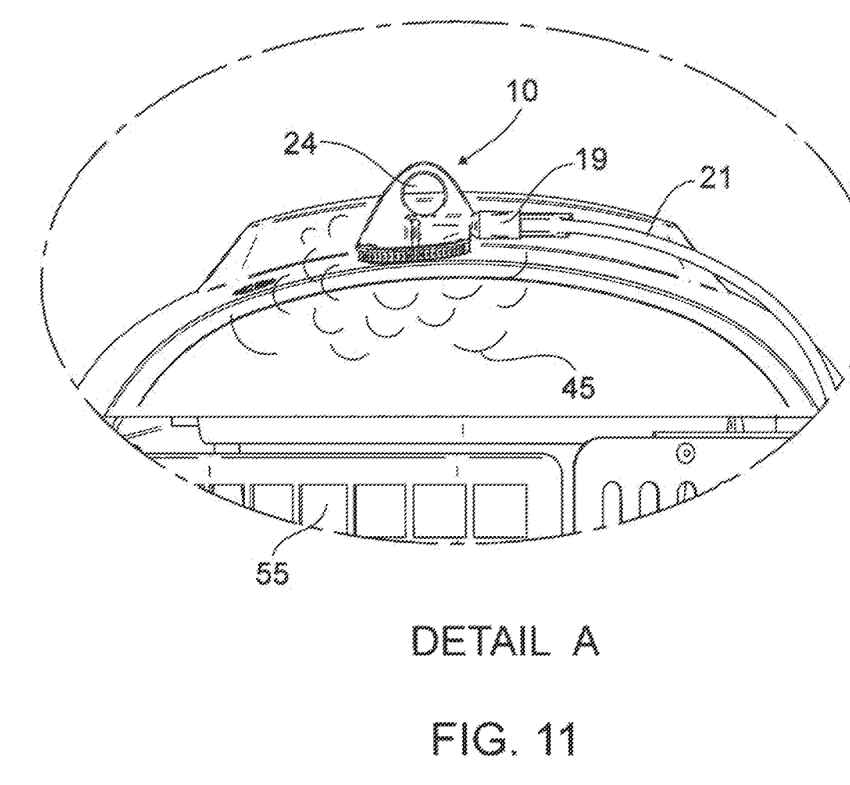
FIG. 11 shows "Detail K of FIG. 10.

This is shown in more detail in "Detail A" shown in FIG. 11 and plumes 45 of carbon dioxide entrained with volatile attractant lure are also shown. Mosquito trap 50 has a cage 55 for attraction of mosquitoes. Trolley 51 has handles 57.

Figure 12:
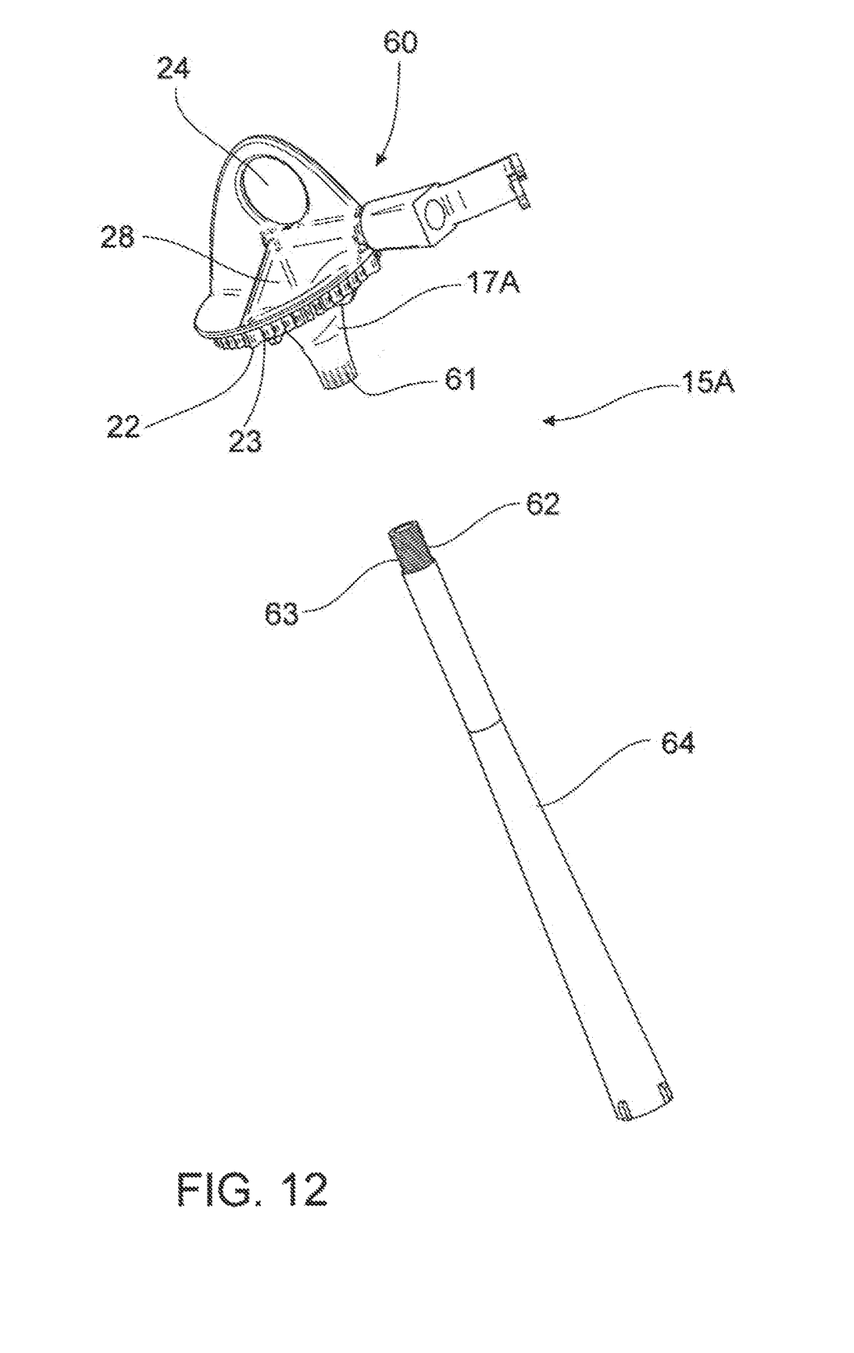
FIG. 12 refers to a different type of modulator to that shown in FIGS. 1 to 2.
Figure 13:
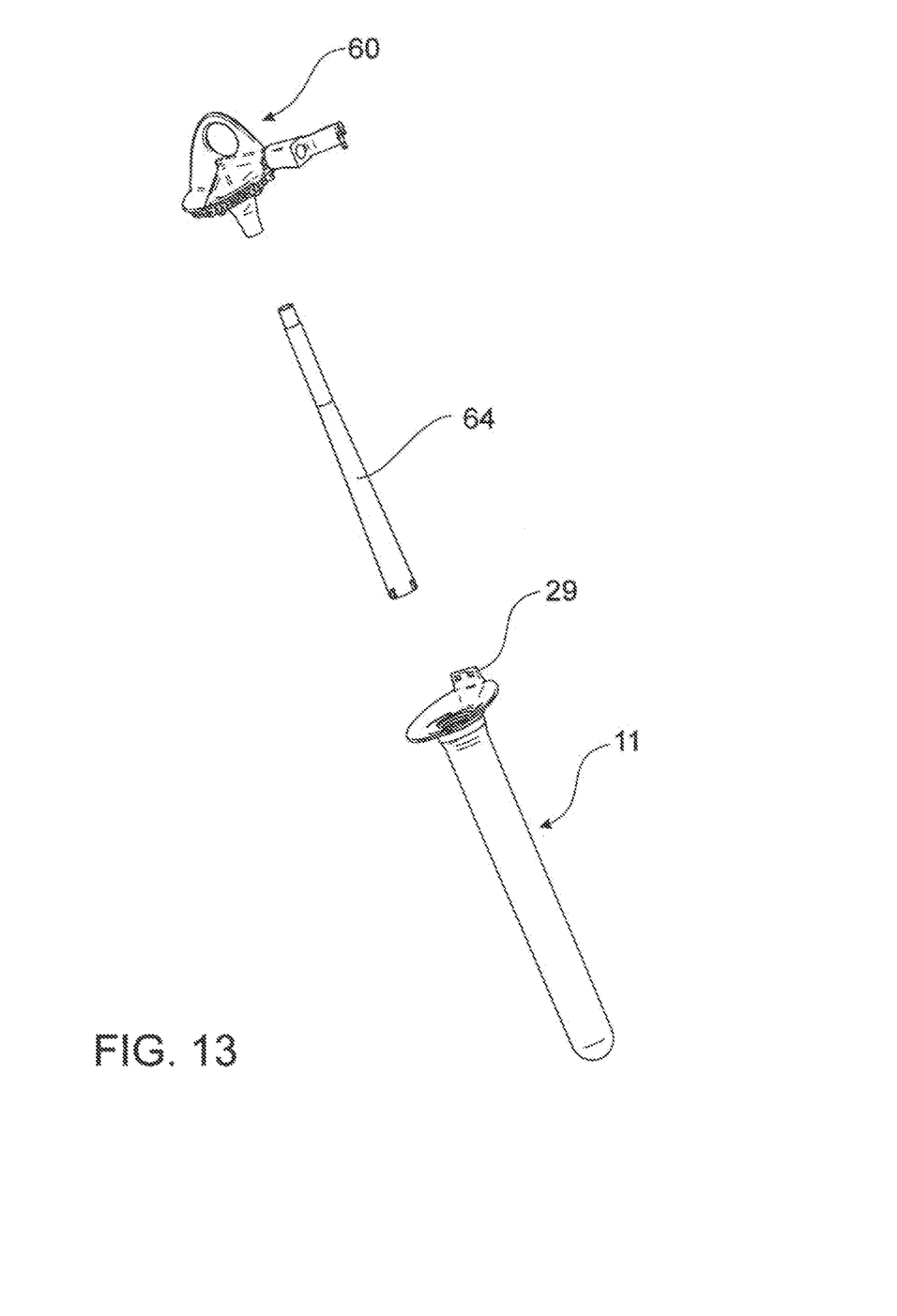
FIG. 13 represents the modulator shown in FIG. 12 about to be inserted into the housing component.

In the drawings shown in FIGS. 12 to 13, there is shown modulator 10A having a head part 60 having a neck portion 17A which has an internal thread 61 shown in phantom for engaging with external thread 62 of spigot part 63 of body part 64 of insertion component 15A which includes both head part 60 and body part 64 as shown in FIG. 12. In FIG. 13 body part 64 is shown being inserted in housing component 11 in a similar manner as shown in FIG. 3.

Figure 14:
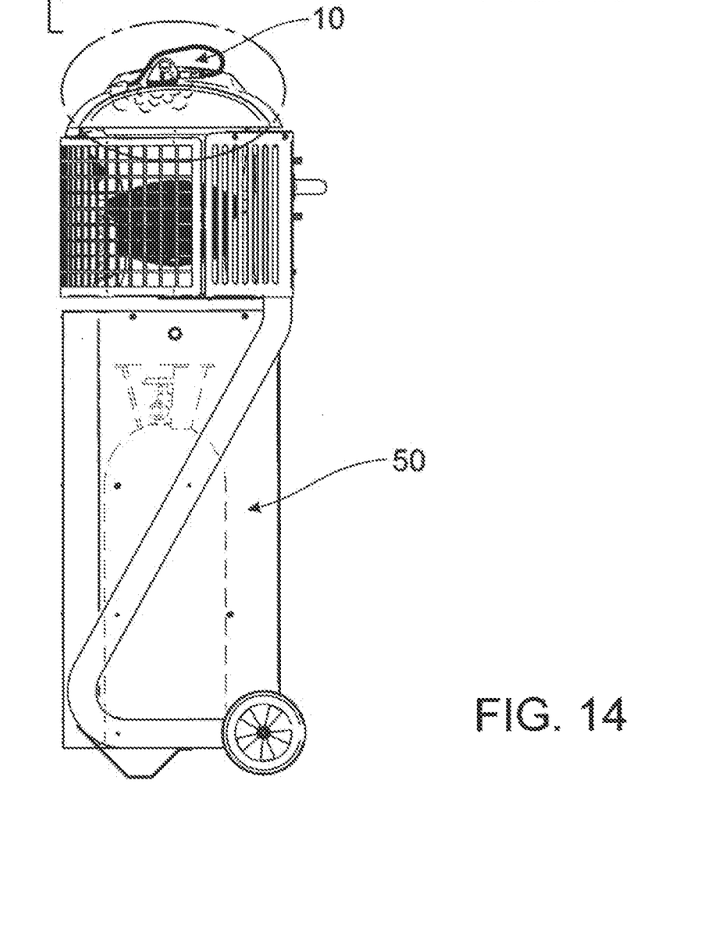
FIG. 14 shows a view of the modulator attached to an insect trap adjacent an exhaust outlet.
Figure 15:
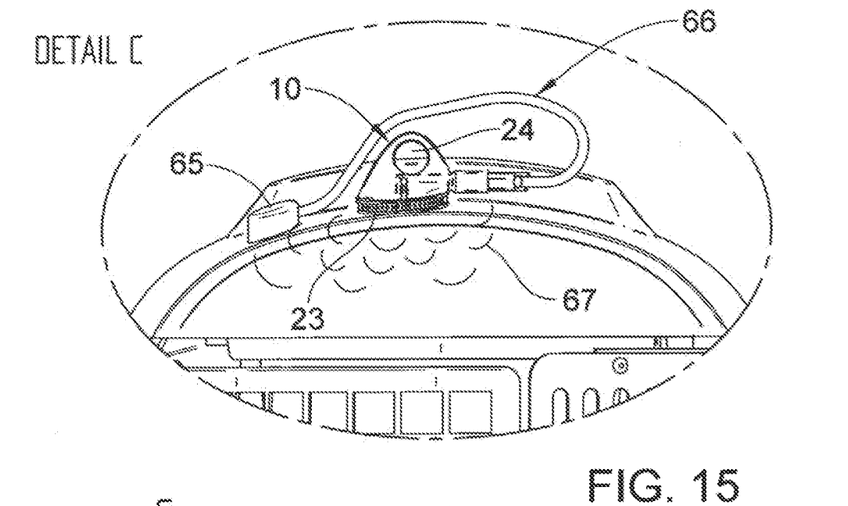
FIG. 15 represents a detail of Detail "C' shown in FIG. 14.

FIGS. 14 to 15 show modulator 10 being attached to a mosquito trap 50 wherein warm, moist air from the exhaust outlet 65 of trap 50 is directed through exhaust hose 66. This results in the evolution of $CO_2$ gas shown by the plumes 67 which is generated within modulator 10 independent of gas bottle 22. The warm moist air from outlet 65 may be used in conjunction with the housing component 11 to cause a reaction with the attractant or viscous medium 14 wherein carbon dioxide is evolved through spaces 23 as shown in FIG. 15.

Figure 16:
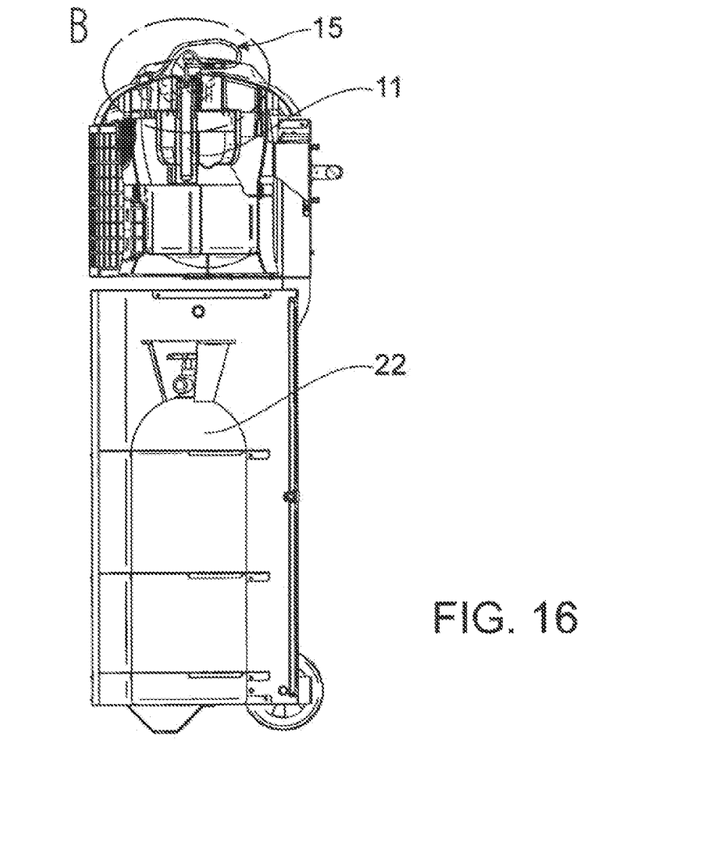
FIG. 16 represents a longitudinal sectional view of the insect trap shown in FIG. 14.
Figure 17:
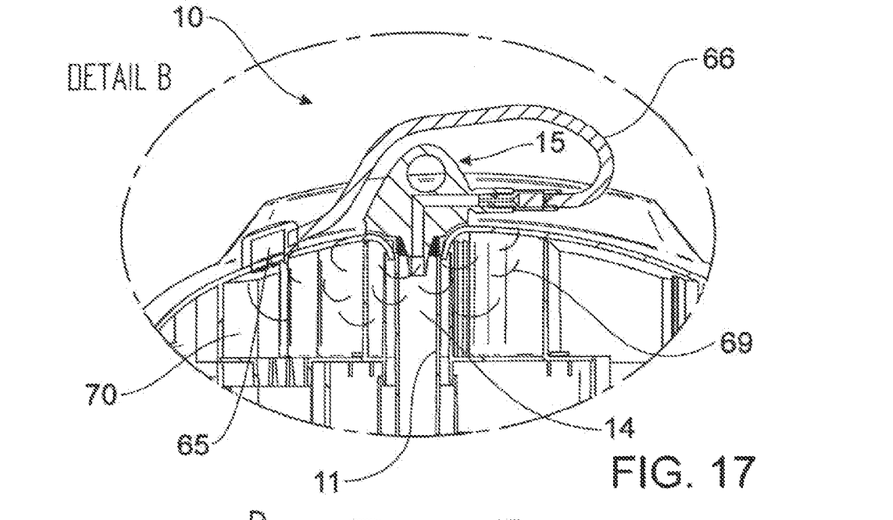
FIG. 17 represents a sectional view of Detail "B" shown in FIG. 16.

FIG. 16 shows a sectional view of FIG. 14 and shows positive pressure and air flow from the plenum chamber exhaust 65 of plenum chamber 70 and there is also shown moist air flow 69 over the internal attractant medium 14 in housing 11.

One example of an attractant formulation within the scope of the invention has the following components all expressed in w/v %, i.e.:

| | | |
|---|---|---|
| (i) | 0.15-8.5% | sugar |
| (ii) | 0.025-0.50% | L-lysine |
| (iii) | 0.1.00-2.5% | valerian powder |
| (iv) | 0.80-2.0% | mushroom extract |
| (v) | 0.80-2.0% | sodium chloride or salt |
| (vi) | 0.40-12.5% | lactic acid; and |
| (vii) | sufficient ammonium bicarbonate or other food grade component acting as a base to provide a pH of 3.0-7.0 whereby each of components (i) to (vi) are dissolved in a solvent which includes cider vinegar, red wine or white wine. | |

The solvent in the insect attractant composition of the invention provides a source of water and alcohol.

Lactic acid may be used as a liquid or a powder. Octenol may also be used which is extracted by alcohol from mushrooms.

The use of sugar in the attractant composition provides a food source to the insect and thus, may be selected from sucrose, fructose, flucose, maltose, caster sugar, confectioner's sugar, brown sugar, maple sugar, honey, Karo syrup, molasses, fruit syrup, corn syrup, cola syrup, maple syrup, beet syrup or other sugars and syrups and mixtures thereof. Other sugars may be utilized if required. The viscosity of the medium and type of constituent employed will control the pulsing rate of gas and also the volume of each pulse.

L-lysine is an amino acid associated with the skin and is believed to have an attraction to insects.

Valerian powder is a source of valeric acid and may be a concentrate of valerian roots and thus may be prepared as described in U.S. Pat. No. 5,211,948. Valeric acid can be an insect attractant because it is a short chain carboxylic acid or volatile fatty acid.

Mushroom extract is a source of octenol which is well known as an insect attractant as set out above. It also contains polysaccharides. It may also function as a food source also for an insect.

Sodium chloride is a component of human sweat which is an insect attractant as set out above and also functions as a preservative for the composition.

Lactic acid is also a well known insect attractant.

Ammonium bicarbonate is a source of ammonia and is also well known as an insect attractant especially when it is combined with other components such as those described in WO 1995/014379, U.S. Pat. No. 6,244,890. U.S. Pat. No. 5,939,062 or EP 0549524. It is preferred that ammonium bicarbonate be added to the insect attractant composition of the invention to produce a pH of 4.5. The amount of ammonium carbonate that may be used is from 0.40% to 3.5%.

The solvent is preferably cider vinegar, red wine or white wine or a mixture thereof and in a preferred embodiment of the invention for a batch of 50×250 ml bottles of attractant composition the following amounts may be utilized:

| | | |
|---|---|---|
| (i) one of | (a) | 4 litres apple cider vinegar |
| | (b) | 4 litres white wine or |
| | (c) | 4 litres red wine |
| (ii) | | 2 cups sugar (i.e. 500 g) and |
| (iii) any two of | (a) | 1 scoop L-lysine (15 g) |
| | (b) | 1 cup valerian powder (150 g) and |
| | (c) | 1000 g mushroom extract |
| | (d) | 1000 g sea salt |
| | (e) | 3 scoops ammonium bicarbonate |

Another example of an attractant formulation failing within the scope of the invention is the following expressed in w/v % i.e.:

| | |
|---|---|
| 10-30% | sugar |
| 40-80% | sodium chloride |
| 5-20% | lactic acid |
| 0.5-5% | valerian powder |
| 1-4% | ammonium bicarbonate | or alternatively, enough ammonium bicarbonate to provide a pH of 3.0-7.0 and more preferably 4.5. Preferably log 10 g-250 g of L-lysine may also be included.

In a preferred embodiment there may be provided a composition having the following components by weight:

| | |
|---|---|
| 66% | salt |
| 20% | sugar |
| 10% | lactic acid |
| 1.5% | ammonium bicarbonate |
| 0.9% | L-lysine |
| 0.9% | valerian powder |

In another preferred embodiment L-lysine may be omitted and the amount of lactic acid may be decreased. Also the amount of ammonia may be increased to make the attractant composition more specific for *Aedes aegypti*. Thus, in this formulation there may be provided:

| | |
|---|---|
| 20-60% | salt |
| 6-20% | sugar |
| 3-10% | lactic acid |
| 20-60% | ammonium bicarbonate |
| 0.5-5.0% | valerian powder |

The above formulations may be tested in a number of traps for efficacy. Thus, the formulations may be tested in an insect trap as described in U.S. Pat. No. 6,655,078 or U.S. Pat. No. 6,145,243 for example.

It therefore will be appreciated from the foregoing that although the above description has concentrated on mainly generation of a pulsed flow of carbon dioxide, it will be appreciated that a pulsed flow of other gases can be produced by the modular of the invention, such as noble gases inclusive of helium and argon or volatile attractant insect lures which may include ammonia, acetone or octenol including 1-octen-3-ol. The modulator of the invention may also generate pulsed flow of pheromones or kairomones which are well known volatile lures for insects. These volatile lures may also be included in the attractant medium or be generated therefrom.

In relation to a gas such as helium or argon, as described above, it may enter the attractant medium which may comprise honey or other viscous material and the gas will only be released from the viscous medium in small bubbles as described above, thereby generating a pulsed flow. The modulator of the invention may also be used to generate a pulsed flow of hydrocarbon fuels inclusive of propane.

From the foregoing it therefore will be appreciated that the modular of the invention is extremely simple in structure and extremely effective in use.

In another aspect of the invention there is provided a method of attracting biting insects which includes the steps of passing a constant flow of carbon dioxide through an attractant medium for insects whereby a mixture of a volatile attractant lure and carbon dioxide is produced after said passage wherein said mixture is caused to be evolved in a pulsed or intermittent flow.

In a further aspect of the invention there is provided a method of attracting biting insects and thus, drawing said biting insects away from a particular location wherein a modulator having an attractant medium for insects having a closure attached thereto is brought to the location and the closure removed to generate volatile attractant lures for attraction of said biting insects.

In a still further aspect of the invention there is provided a method of converting a constant flow of gas to a pulsed or intermittent flow of gas which includes the step of passing said constant flow of gas through a viscous medium wherein said gas is released from the viscous medium in small bubbles thereby generating said pulsed or intermittent flow.

The invention claimed is:

1. A modulator for changing a constant flow of gas to a pulsed or intermittent flow of gas, said modulator including an inner tube and a housing component surrounding the inner tube to define an outer passage which is constituted by a peripheral gap between the inner tube and an internal surface of the housing component and said outer passage is in flow communication with an outlet of the modulator wherein gas is generated either in situ within a hollow interior of the modulator which contains a viscous medium and be caused to flow out of the outlet in a pulsed or intermittent flow or alternatively gas is passed into the modulator in a constant flow and upon reaching the hollow interior passes through the viscous medium and subsequently through the outer passage and then through the outlet in a pulsed or intermittent flow.

2. The modulator as claimed in claim 1, wherein the inner tube is constituted by an insertion tube for insertion into a hollow bore of the housing component.

3. The modulator as claimed in claim 2 wherein the housing component is a hollow tube having one closed bottom end and an open upper end in use.

4. The modulator as claimed in claim 3, wherein the open end of the hollow tube has a lid or cover releasably attached to the open end for preventing escape of the gas when not in use.

5. The modulator as claimed in claim 1, wherein a bottom part of the housing component contains the viscous medium into which the gas penetrates which is released therefrom in small bubbles or pulses.

6. The modulator as claimed in claim 1, wherein the housing component has an elongate body which tapers outwardly from top to bottom.

7. The modulator as claimed in claim 2, wherein the insertion tube has a bottom open end.

8. The modulator as claimed in claim 2, wherein the insertion tube has a top end in use which has a plurality of ribs having spaces or gaps therebetween constituting said outlet which is in flow communication with a hollow interior of the insertion tube.

9. The modulator as claimed in claim 1, wherein the viscous medium has a viscosity of from 500-30,000 cP.

10. The modulator as claimed in claim 1, wherein the viscous medium is formed of food grade components and is responsible for causing generation of a volatile insect lure consisting of or inclusive of carbon dioxide.

11. The modulator as claimed in claim 10, wherein there is provided adjacent the outlet a connection device for connection to a gas hose in fluid communication with a source of carbon dioxide.

12. The modulator as claimed in claim 11, wherein the connection device includes a plug-socket connection to the gas hose.

13. The modulator as claimed in claim 12, wherein there is provided a retaining clip adjacent the connection device for engagement with the gas hose.

14. The modulator as claimed in claim 2, wherein the housing component is provided with a plug-socket connection to the insertion tube.

15. The modulator as claimed in claim 14, wherein the housing component is provided with a projection having apertures which engage with corresponding tabs of the insertion tube.

16. The modulator as claimed in claim 2, wherein the insertion tube is provided with one or more flow passages in fluid communication with said gas when the modulator is connected to a gas source.

17. A modulator as claimed in claim 2 wherein the insertion tube has a head part incorporating said outlet and a body part for releasable attachment to the head part.

18. An assembly of an insect trap and a modulator as claimed in claim 1, wherein the modulator is attached to a top wall or top part of the insect trap for dispensing carbon dioxide entrained with attractant lure for biting insects which is discharged into a chamber of the insect trap.

19. An assembly as claimed in claim 18 also including a gas bottle located on a trolley which also supports the mosquito trap, wherein the gas bottle is in flow communication with the modulator for producing a constant flow of carbon dioxide.

* * * * *

UNITED STATES PATENT AND TRADEMARK OFFICE
CERTIFICATE OF CORRECTION

| | | Page 1 of 1 |
|---|---|---|
| PATENT NO. | : 8,621,778 B2 | |
| APPLICATION NO. | : 13/056630 | |
| DATED | : January 7, 2014 | |
| INVENTOR(S) | : Andrew Coventry | |

It is certified that error appears in the above-identified patent and that said Letters Patent is hereby corrected as shown below:

On the Title page of the patent, item (22) currently reads "Filed: Jan 28, 2011" and should read
-- PCT Filed: July 29, 2009 --.

On the Title page of the patent, prior to item (65), the following is inserted:
    -- (86) PCT No.: PCT/AU2009/000964
        § 371 (c)(1), (2), (4) Date: January 28, 2011

(87) PCT Pub. No.: WO2010/012031
        PCT Pub Date: February 4, 2010 --.

On the Title page of the patent, please delete item "(63)".

On the Title page of the patent, please delete item "(30)".

Signed and Sealed this
Twenty-ninth Day of April, 2014

Michelle K. Lee
*Deputy Director of the United States Patent and Trademark Office*